United States Patent [19] [11] 4,427,781
Masson et al. [45] Jan. 24, 1984

[54] PARTICLE AGGLUTINATION IMMUNOASSAY WITH AGGLUTINATOR FOR DETERMINING HAPTENS; PACIA

[75] Inventors: Pierre L. Masson, Brussels; Daniel Collet-Cassart, Limal; Carl G. Magnusson, Brussels, all of Belgium

[73] Assignee: International Institute of Cellular and Molecular Pathology, Belgium

[21] Appl. No.: 358,566

[22] Filed: Jan. 24, 1984

[30] Foreign Application Priority Data

Mar. 16, 1981 [GB] United Kingdom ............... 8108112

[51] Int. Cl.$^3$ ............................................ G01N 33/54
[52] U.S. Cl. .................................... 436/509; 436/534; 436/805; 436/815; 436/821; 436/825
[58] Field of Search ................. 23/915; 436/509, 534, 436/815, 821, 825

[56] References Cited

U.S. PATENT DOCUMENTS 4,162,895  7/1979  Cambiaso .......................... 23/915 X
4,184,847  1/1980  Hallgren ........................... 23/915 X
4,279,617  7/1981  Masson ............................. 23/915 X
4,308,026 12/1981  Mochidd ........................... 23/915 X

OTHER PUBLICATIONS

Chemical Abstracts, 95: 146230h, (Oct. 26, 1981).
"Immunoassays for the 80's", A. Voller et al., Eds., pp. 35–41, University Park Press, Baltimore, (1980).

Primary Examiner—Sidney Marantz
Attorney, Agent, or Firm—S. P. Tedesco; C. J. Herron

[57] ABSTRACT

A particle counting assay for haptens (small non-protein monovalent substances having a molecular weight below 1500) comprises mixing a liquid sample (e.g. of human origin) containing the hapten, with finely divided inert particles bearing the same hapten (or a specific analogue thereof), an agglutinator such as RF or C1q, and a measured amount of antibody, which amount is insufficient to cause agglutination of all the particles. The amount of hapten is determinable by measuring the extent of the agglutination.

10 Claims, 3 Drawing Figures

PARTICLE AGGLUTINATION IMMUNOASSAY WITH AGGLUTINATOR FOR DETERMINING HAPTENS; PACIA

This invention relates to a particle agglutination assay which is especially suitable for the analysis of haptens.

In this specification, the term "antigen" excludes haptens, i.e. excludes small non-protein substances which are monovalent and have a molecular weight below about 1500.

There are various known immunoassays based on particle agglutination techniques. Essentially, such assays depend for their qualitative or quantitative results upon the presence and/or extent or agglutination of finely divided particles which carry an immunoreactive reagent. The most commonly used particles are the so-called latex particles which are commercially available and generally used in a microscopic or sub-microscopic size i.e. up to about 15 microns, most usually of the order of a few microns or sub-micron in size. In some assays, the presence of agglutinates can be observed with the naked eye, but for quantitative results it is normal to count (or otherwise assess) the number of particles (usually the number of unagglutinated particles) in the final reaction mixture. Immunoassays based on particle agglutination techniques are described in our U.K. Pat. No. 1508133, U.S. Pat. Nos. 4,162,895, 4,184,849 and 4,062,935, and European patent publication No. 0010932, to which reference should be made for further details.

A particle agglutination assay for antigens and haptens is described in our U.S. Pat. No. 4,184,849. This assay uses two different particulate reagents which mutually agglutinate when mixed together, but whose agglutination is inhibited by the presence of the antigen or hapten under assay. Whilst this assay is very satisfactory in practice, it has the disadvantage of requiring two different particulate reagents, each specific to the particular assay being performed, and each being used in controlled amounts. The use of two such reagents increases the complexity of the overall procedure and is, from this point of view, undesirable.

There is one known particle-based agglutination assay for antigens which uses only one particulate reagent, but the assay is not satisfactory for haptens. In this assay (see, for example, Methods in Enzymology, vol. 74, pp. 106–139, 1981, J. J. Langone (Ed.), Academic Press, New York), the sample containing the antigen under assay is mixed with latex bearing an antibody, and the antigen binds to antibody and causes agglutination of the latex particles. This agglutination occurs because the antigen is multivalent and hence can simultaneously bind to two or more antibody molecules, thus bridging two (or more) latex particles. By contrast, haptens are monovalent and whilst they become bound to the antibody on the latex, they cannot bridge between two or more latex particles and so cause agglutination.

Another type of particle agglutination assay, which uses only one particulate reagent, is known for the assay of immune complexes (see Methods in Immunology, supra). In this assay, the sample (containing immune complexes to be assayed) is mixed with immunoglobulin G-coated latex particles and a limited amount of an agglutinator. Competition for reaction with the agglutinator occurs between the latex-IgG and the free complexes, and the amount of complexes in the sample can be determined from the degree of agglutination of the particles. This method of assay is very sensitive, rapid and precise. In principle, a similar procedure could be used to assay antigens, by mixing the sample (containing the antigen under assay) with latex particles bearing the same antigen, and an excess of antibody. Both the free and the latex-bound antigen would then bind to antibody to form complexes, and by adding a limited amount of agglutinator, agglutination of the particles will occur to an extent dependent on the amount of antigen present in the original sample.

Whilst such an assay is, in theory, possible for antigens, it will be unsatisfactory for haptens because whilst they will bind to the antibody to form complexes, the free complexes will have only a very weak affinity for the agglutinator. Further, even if such an assay would work for haptens, there is a further disadvantage in that the agglutinating quality of agglutinators varies greatly according to source, so that the use of a critical quantity can give rise to diffilculties in reproducibility, particularly where a large number of assays are to be performed on a commercial scale.

We have now devised a particle agglutination assay for haptens which involves the use of only one latex particle reagent, and which does not rely on the use of critical quantities of agglutinator. In particular, we have found that whilst free hapten-antibody complexes have a very weak affinity for agglutinator, that affinity can surprisingly be markedly increased if the hapten is first bound to a latex particle, e.g. conjugated to a carrier such as a protein or polymer, and then coupled to the latex, or coupled directly to the latex. The strength of the bond then formed between the latex-bound complex and the agglutinator is, we have found, sufficient to cause two latex particles (each bearing complex) to become bound together by the agglutinator. This is in marked contrast to the effect of agglutinator on free hapten-antibody complexes, where the affinity between the agglutinator and the complexes is too weak to cause any significant binding.

Using this unexpected result, it is possible to assay a hapten as follows. The sample containing the hapten under assay is mixed with latex (or other particles) bearing the same hapten as is under assay or a specific analogue thereof, and a limited amount of antibody. The free hapten and the latex-bound hapten compete for the limited quantity of antibody, forming complexes therewith, one portion of the antibody becoming bound to free hapten and another portion becoming bound to the latex-bound hapten. An agglutinator is also included in the mixture and this causes agglutination only of those latex particles bearing the hapten-antibody complex. The agglutinator does not bind to any significant extent with either the latex-hapten, or the free hapten, or the free hapten-antibody complexes. The presence and extent of agglutination indicates the presence and amount of the hapten under assay.

In this assay of haptens, the amount of agglutinator required is merely that amount necessary to cause sufficient agglutination of the latex-complex particles. Since, in fact, no other component of the hapten assay reaction mixture has any very significant binding capacity for the agglutinator, very little agglutinator is in practice necessary. Accordingly, the method of the invention has the advantage of very economic use of an expensive reagent in the assay of haptens. Further, the use of a critically determined amount of agglutinator is completely avoided; the competition reaction occurs not in respect of the agglutinator (which is inevitably of variable quantity), but rather in respect of the antibody. The production of reproducible antisera is a well established procedure.

According to the invention, there is provided a method of assaying a hapten in a liquid sample, which comprises mixing with the liquid sample:

(a) finely divided inert particles bearing the same hapten as is under assay, or a specific analogue thereof;

(b) a "limited amount" (as hereinafter defined), of antibody against the hapten;

(c) an agglutinator;

and measuring the extent of agglutination and therefrom determining the amount of hapten in the liquid sample.

Whilst we do not wish to be bound by this theory, and the invention is not limited thereto, we believe that the increased affinity of latex-bound hapten-antibody complex (over free hapten-antibody complex) for agglutinator results from the presence, in close proximity on the latex surface, of several hapten molecules each of which may bind to antibody, resulting in the possibility for the agglutinator to bind by two or more linkages to each latex particle (via the antibody thereon). Thus, the increase in affinity between the agglutinator and the complexes when the latter are bound to latex arises, we believe, from the establishment of a multivalent region on the particle surface for binding with agglutinator. Such multivalent regions do not occur, of course, in dilute solutions of free hapten-antibody complex. In effect, by immobilising hapten on a latex surface, the hapten-antibody complexes are "concentrated", so providing an increased affinity for agglutinator.

In the method of the invention, a "limited amount" of antibody is that quantity of antibody which when added to a latex-hapten agglutination reaction mixture, causes less than 100% agglutination, a preferred value being from 40% to 80%, most preferably between 70 and 80%, agglutination. The concentration of latex-hapten is itself preferably adjusted so that approximately 50% of the particles are agglutinated when added to a solution of approximately 50% of the expected assay range concentration of antigen or hapten, with the agglutinator in excess (i.e. ±10% change of agglutinator concentration causes no appreciable change in measured concentration of unagglutinated particles).

In order to achieve a result in this preferred range, some preliminary trial and experiment will usually be necessary in respect of each hapten to be assayed, but in fact such experiment is always involved in order to establish a standard curve (or other standard results) whereby an absolute value for the amount of hapten under assay can be established from a reading of the extent of agglutination. Such preliminary tests may also be used to establish the optimum amount of agglutinator for any particular assay.

The method of the invention is of broad utility. Particular haptens which can advantageously be assayed by the method include drugs and drug metabolites such as theophylline, barbitone, phenylhydantoin, digoxin, digitoxin and gentamicin; intracellular messenger such as cyclic AMP and cyclic GMP, prostaglandins and prostaglandin metabolites; hormones such as hypothalmic and pineal hormones, e.g. thyrotropin releasing hormone, gonadotropin releasing hormone, somatostatin, melatonin, substance P, neurotensin; pituitary hormones, e.g. oxytocin and vasopressin; thyroid hormones, e.g. thyroxine and triiodothyronine; hormones of the gastrointestinal tract, e.g. gastrin, secretin, cholecystokinin and serotonin; pancreatic hormones, e.g. glucagon and C-peptide; and steroid hormones, e.g. estradiol, progesterone, testosterone, aldosterone and cortisol; vitamins such as B12, folic acid, vitamin D metabolites; and haptens of bacteriological or virological origin, e.g. the glycolipid of leucosis virus. The liquid to be assayed for a particular hapten will usually be of biological origin, e.g. human or animal body fluids such as blood serum, saliva or urine.

The particulate reagent will normally be latex particles as described hereinbefore, but other particles (whilst not preferred), such as agarose gel, Sephadex gel or bentonite, could be used. The particles bear the same hapten as is under assay or a specific analogue thereof. The preparation of hapten-bearing particles is well known in the art. Sometimes, the hapten can be absorbed by a suitable coating on the particles, or it may be chemically coupled thereto by a bridging agent. In a few instances, hapten can be coupled directly to the polymer of the latex particle itself. The method of preparation of the hapten-bearing particles is not important, provided that the bound hapten is accessible to antibody.

The antibody used in the method of the invention may be raised in conventional manner.

The agglutinator is preferably rheumatoid factor (RF), but other agglutinators such as a component of complement called Clq, mouse serum and acitic fluid, can be used. These agglutinators are described in our patent specifications referred to hereinbefore. In the assay of haptens, the agglutinator functions to cause agglutination of those partilces on which antibody has become bound to the hapten. The other particles, bearing hapten alone, are not agglutinated. The agglutinator will not react to any significant extent with the free hapten-antibody complexes.

It is well known that, in immunoassays, interferences can arise particularly (in the case of liquids of biological origin) from non-specific protein-protein interactions. As described in our European patent application published under the No. 0038181, such interactions can be reduced by the use of chaotropic agents, and such agents can be used in the method of the present invention. Another technique for avoiding protein interferences involves treating the liquid sample (prior to assay) with a protease enzyme (e.g. pepsin) to digest the unwanted or interfering proteins. This technique is described in our European patent application No. 81305261.0.

In the method of the invention, the presence and/or amount of the hapten under assay is determined from the presence and/or extent of agglutination and by reference to standard results. In assessing whether, and to what extent, any agglutination has occurred, we prefer to count the number of particles remaining unagglutinated in the reaction mixture. Such selective counting can be effected automatically using for example, a Technicon Autocounter system or similar system. (The words "Technicon" and "Autocounter" are trade marks.) Whilst selective counting is preferred, an assessment of the extent of agglutination can be made in other ways, such as by separating the agglutinates from the unagglutinated particles and weighing or otherwise measuring the quantities.

The method of the invention can be effected manually or by a continuous procedure such as the Technicon PACIA technique.

In order that the invention may be more fully understood, the following example of the assay of digoxin is given by way of illustration only.

In the Example, reference is made to the accompanying drawings, wherein.

EXAMPLE

A. Reagents

Figure 1:
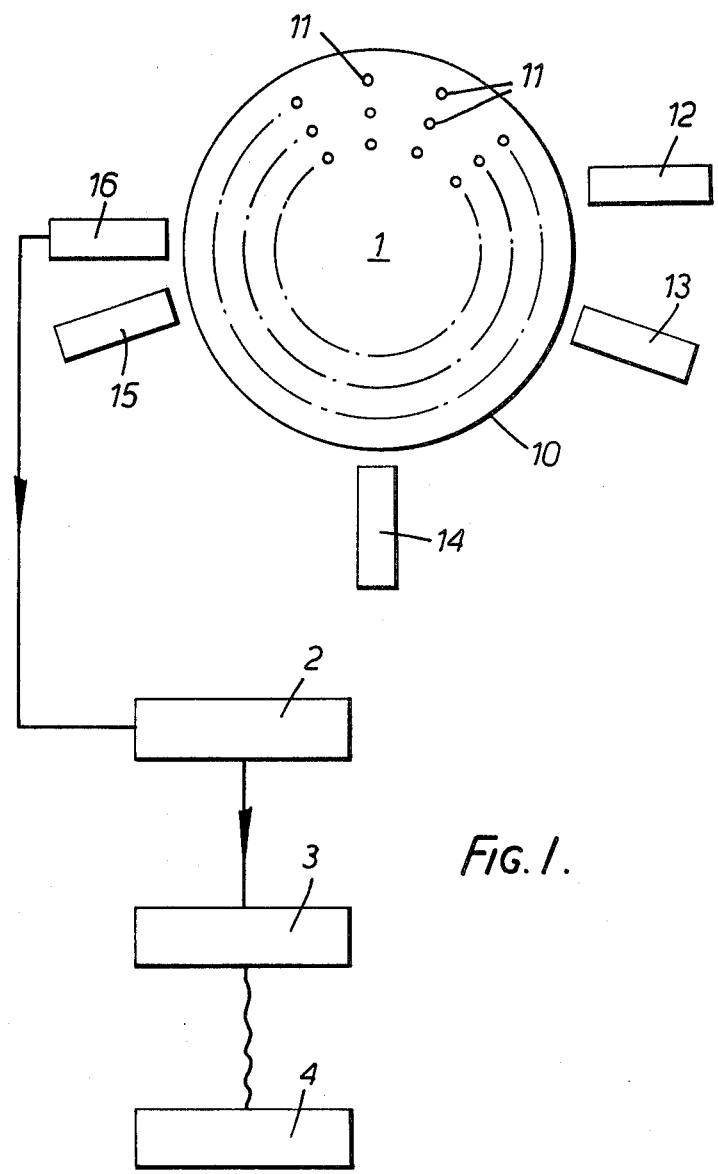
FIG. 1 is a simplified schematic diagram illustrating one form of apparatus for carrying out the method of the invention.

Glycine buffered saline (GBS), 0.1 M NaCl, 0.17 mol/L glycine, 0.04 g/L Na azide, pH adjusted to 9.2 with NaOH.

GBS-BSA, 10 g/L bovine serum albumin (Biograde from Calbiochem, San Diego, Calif.) in GBS.

HCl-pepsin, 0.15 mol/L HCl containing 4 g/L pepsin twice crystallised (from Sigma Chemical Co., St. Louis, Mo.). This solution kept at 0°–4° C. is stable about one day.

IgG anti-digoxin. IgG was extracted by Rivanol precipitation from a rabbit antiserum prepared against a digoxin-bovine fibrinogen conjugate. One ml of this antiserum was sufficient for 250,000 assays.

RF. Whole serum of a rheumatoid patient undergoing plasmapheresis, with a latex agglutination titer (latex-RF reagent, Behringwerke AG. Marburg/Lahn, West Germany) of 1/3000.

Agglutinating mixture. The anti-digoxin IgG was mixed with RF and GBS-BSA to reach a final titer of 1/50 for RF and 1/4000 of the concentration of IgG in the starting antiserum. The mixture was stored at −20° C. in 1 ml aliquots, enough for 60 assays.

Latex. 0.8 $\mu$ carboxylated polystyrene particles (10% w/v - Estapor K150, lot No. 314).

BSA-digoxin conjugate. prepared by the periodate procedure.

Digoxin-BSA-latex. Five hundred $\mu$l of carboxylated latex were washed in 5 ml of 0.02 mol/L borate buffered saline, pH 8.1 (BBS), centrifuged, resuspended in 1 ml BBS, and activated by 45 min stirred incubation at room temperature with 25 mg of 1-ethyl-3 (3-dimethylamino-propyl)-carbodiimide HCl. After centrifugation and resuspension in 1 ml BBS, the activated latex was incubated over-night at 4° C. under gentle agitation with 25 $\mu$l of a 10 g/L solution of BSA - digoxin conjugate in 9 g/L saline. After addition of 250 $\mu$l of GBS-BSA the particles were centrifuged, washed three times with GBS-BSA, resuspended in 10 ml GBS-BSA, and sonicated for a few seconds in a Branson Sonifier B12. If to be used within 3 weeks, the digoxin-BSA-latex was stored at 4° C. For longer storage, the reagent was lyophilised without any further treatment. Before use, the latex suspension was diluted ¼ with GBS containing 5 mM EDTA, 60 g/l polyethylene glycol 6000 (Merck, Darmstadt, West Germany) and NaCl at half saturation.

B. Standards and samples

Digoxin was dissolved in ethanol to a concentration of 1 g/L. To prepare the standards, this solution was then diluted with a pool of normal human sera. Chylomicrons usually do not interfere in the latex counting. However, when the serum samples have been frozen, some particles formed by denatured lipoproteins can be counted as if they were latex particles. As most of the present work was done on sera which had been frozen, they were first treated to eliminate this possible source of interference. Samples of about 200 $\mu$l were mixed with 100 $\mu$l of Freon 113 (Serva, Heidelberg, W. Germany) while vortexing and then centrifuged for 5 min at 5000 rev/min. For protease digestion of the samples (to destroy proteins), aliquots of about 100 $\mu$l of the clear supernatants were incubated for 10 min at 37° C. with 300 $\mu$l HCL-pepsin. The digestion was then stopped by addition of 20 $\mu$l of 2 mol/l TRIS (tris(hydroxymethyl)-methylamine). Protease digestion was also applied, in exactly the same manner, to the standards.

C. Equipment

The experiments were conducted using a Technicon PACIA automated system. The system is described in the literature (see, for example, "Methods in Enzymology" cited above), but a simplified diagram thereof is shown in FIG. 1 of the accompanying drawings. Referring to FIG. 1, the system comprises essentially four components, a DIAS component 1, a pump 2, an autocounter 3 and an electronics module 4. The DIAS component 1 (DIAS means diluter-incubator-agitator-sample) comprises a horizontal circular tray 10 mounted for rotation about a vertical axis, and having a series of apertures therein receiving sample tubes 11. Around the periphery of tray 10 are arranged stations 12,13,14,15 including probes for adding quantities of reagents to individual tubes. The tubes 11 depend below tray 10 into a temperature-controlled chamber. At a further station 16, the final reaction mixture is sampled and the sample passes through a manifold in which it may be further diluted and debubbled, for example, and via pump 2 to autocounter 3 for counting unagglutinated particles only. Module 4 prints out, or otherwise indicates, the results. In DIAS component 1, the sample tubes 11 are agitated to keep the particles in suspension.

D. PACIA method

An unmeasured quantity, approximately 200 $\mu$l, of treated serum was pipetted into a sample tube 11 and placed in the inner row of the sampler tray. A probe from station 12 aspirates 100 $\mu$l of the sample into another sample tube (called a reaction tube), then 15 $\mu$l of the agglutinating mixture and 15 $\mu$l of latex conjugate were sequentially added at stations 13 and 14. After incubation at 37° C. for 25 min in the vortexing tray, the suspension was diluted (station 15) by addition of 0.88 ml of GBS and 88 $\mu$l was aspirated (station 16) into a manifold in which the suspension was further diluted 20 times with GBS containing 1 ml/L Tween 20. After debubbling, the resulting stream passed through the optical cell counter (3). The concentration of unagglutinated particles was expressed by peak heights on the recorder. Fifty analyses/h were performed on this apparatus.

The preliminary pepsin digestion of the samples was done manually.

E. Radioimmunoassay (RIA) (for comparison)

RIA was performed with IMMOPHASE kits from Corning Medical, Corning Glass Works, Medfield, Mass., U.S.A.

F. Results

Figure 2:
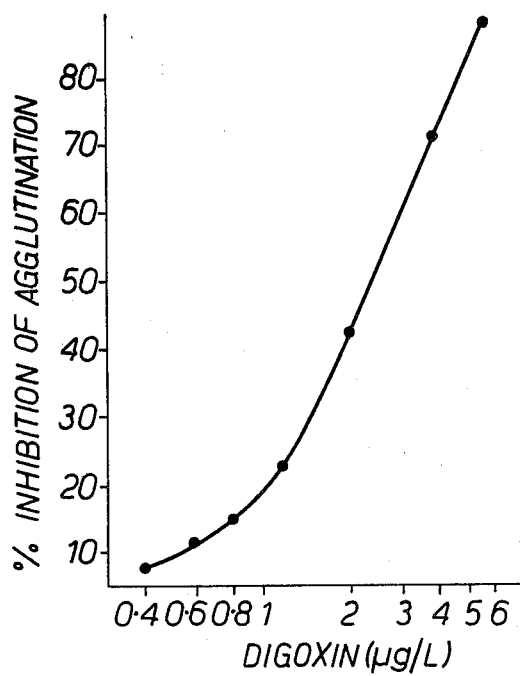
FIG. 2 is a graph of % inhibition of agglutination plotted against the amount of digoxin (ug/1), i.e. a calibration curve for determination of digoxin by PACIA.

Calibration curve. To achieve high sensitivity, we used the highest dilution of anti-digoxin IgG (1/4000) which gave in the presence of RF a reduction of the number of particles to at least 30% of the total number of particles obtained in the absence of agglutinators. The addition of increasing amounts of digoxin caused a progressive increase in the number of unagglutinated particles (FIG. 2). The small peaks obtained in the absence of digoxin varied slightly from day to day. Hence to obtain similar calibration curves we expressed the extent of the reaction as a percentage of the total inhibition corresponding to the difference between the peak height obtained in the absence of agglutinator and peak height in the absence of inhibitor. The calibration curve extended from 0.4 µg/L to 6 µg/L.

Interferences. To check for possible interferences by non-specific agglutinators resisting the preliminary pepsin treatment, we tested the agglutinating activity of 49 patients' sera on digoxin-BSA-latex, the agglutinating mixture being replaced by the buffer usually used to dilute the anti-digoxin IgG and RF. The CV for the mean concentration of non-agglutinated particles was 1.7%. We also tested for possible non-specific inhibitory effects on the agglutination produced by the mixture of anti-digoxin IgG and RF using 11 other different patient's sera which were devoid of digoxin. The CV for the mean peak height was 3.7%.

Recovery. Digoxin was added to 100 sera in increasing amounts to produce 10 concentration levels ranging from 0.6 µg/L to 5.8 µg/L (Table 1). The correlation between the PACIA results and the known values was r=0.989 (y=0.07+1.03 x).

Figure 3:
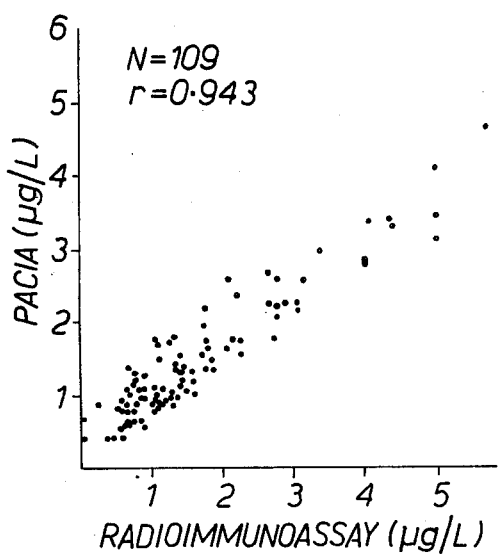
FIG. 3 is a plot showing the correction between the assay results determined by the PACIA method against those determined (on the same samples) by radioimmunoassay (N=109, r=0.943).

Correlation with RIA. One hundred and nine sera were assayed in duplicate by PACIA and the means of the two results were used for corelation with RIA (FIG. 3). The coefficient for values between 0 and 5.7 µg/L was r=0.943 (PACIA results=0.37+0.68 RIA results).

Precision. The intra- and interassay precisions were studied using samples with concentrations covering most of the range of the therapeutic values (Table 2). Maximal intra-assay and interassay CV were 12.5% and 8.9%, respectively. The relatively high intra-assay CV can be explained for one series of assays by drift. For example, the results obtained for the sample spiked with 1.10 µg/L (CV=10.9) increased linearly with time from 0.93 µg/L to 1.30 µg/L. However, in other series the drift was less evident and the imprecision was caused by a few assays only; for example, in the 1.25 µg/L sera (CV=12.0), three results were 1.60 µg/L, 1.60 µg/L and 1.55 µg/L.

TABLE 1

| Recovery of digoxin by PACIA | | |
|---|---|---|
| Added (µg/L) | Recovered (µg/L ± SD) | Recovery (% + SD) |
| 0.60 | 0.615 ± 0.059 | 102.5 ± 9.8 |
| 1.13 | 1.151 ± 0.068 | 101.8 ± 6.0 |
| 1.75 | 1.736 ± 0.159 | 99.2 ± 9.1 |
| 0.70 | 0.810 ± 0.092 | 115.7 ± 13.1 |
| 1.42 | 1.423 ± 0.173 | 100.2 ± 12.2 |
| 1.95 | 1.928 ± 0.102 | 98.9 ± 5.2 |
| 2.90 | 2.968 ± 0.289 | 102.3 ± 10.0 |
| 3.80 | 3.937 ± 0.326 | 103.6 ± 8.6 |
| 5.20 | 4.768 ± 0.304 | 91.7 ± 5.8 |
| 5.80 | 5.788 ± 0.259 | 99.8 ± 4.5 |

The starting solutions of digoxin were prepared in a pool of normal sera and 1 vol was added to 9 vol of each of the various sera to be tested. The recovery was calculated on 10 different sera for each concentration of digoxin. The first three groups were made with the same 10 sera, whereas the seven other groups were made with different sera.

TABLE 2

| Precision of the determination of digoxin by PACIA | | | |
|---|---|---|---|
| Mean concentration (g/L ± SD) | Intra-assay CV[a] (%) | Mean concentration (g/L ± SD) | Interassay CV[b] (%) |
| 0.96 ± 0.12 | 12.5 | 0.75 ± 0.06 | 8.4 |
| 1.10 ± 0.12 | 10.9 | 1.49 ± 0.13 | 8.9 |
| 1.25 ± 0.15 | 12.0 | 2.92 ± 0.17 | 5.8 |
| 2.97 ± 0.13 | 4.4 | | |

[a]Twenty assays repeated within a day with one calibration curve.
[b]Assay repeated during 20 days with the same latex preparation. Sera were spiked with digoxin.

We claim:

1. A method of assaying a hapten in a liquid sample, which comprises mixing with the liquid sample (i) finely divided inert particles bearing a reagent, (ii) an agglutinator and (iii) at least one other reagent, and determining the presence and/or amount of said hapten from the extent of agglutination of the particles, wherein:
   (a) the finely divided particles bear the same hapten as is under assay, or a specific analogue thereof;
   (b) said other reagent is an antibody against said hapten;
   (c) the amount of said antibody added to the mixture is less than the amount required to cause 100% agglutination of the particles; and
   (d) the agglutinator causes agglutination of hapten- or hapten analogue-bearing particles on which the antibody has formed a complex with said hapten or hapten analogue and does not cause agglutination of uncomplexed particles, uncomplexed hapten or free hapten-antibody complexes.

2. A method according to claim 1, wherein the amount of antibody is such as to cause from 40 to 80% of the particles to become agglutinated.

3. A method according to claim 1, wherein the extent of agglutination is measured by counting the unagglutinated particles.

4. A method according to claim 1, wherein the hapten is selected from drugs, drug metabolites, intracellular messengers, hormones, vitamins, and haptens of bacteriological or virological origin.

5. A method according to claim 1, wherein the liquid sample is a human or animal body fluid.

6. A method according to claim 1, wherein the agglutinator is RF, C1lq, mouse serum or ascitic fluid.

7. A method according to claim 1, wherein the hapten under assay is a non-protein but wherein the liquid sample contains one or more proteins capable of interfering in the assay, wherein a protease enzyme is added to the liquid sample to digest said one or more proteins to remove their interfering effects.

8. A method according to claim 1, wherein one or more chaotropic agents are also added to said sample to reduce the effects of non-specific protein-protein interactions interfering in said assay.

9. A method of assaying a human body fluid sample for a hapten selected from the group consisting of drugs, drug metabolites, intracellular messengers, hormones, vitamins, haptens of bacteriological origin and haptens of virological origin, which method comprises forming a mixture of
   (1) the liquid sample;

(2) finely divided inert particles bearing the same hapten as is under assay or a specific analogue thereof;

(3) an agglutinator selected from RF, C1q, ascitic fluid and mouse serum; and (4) a quantity of antibody against said hapten, which quantity causes from 40 to 80% of the said inert particles to agglutinate;

incubating the mixture so formed; counting the number of particles remaining unagglutinated and therefrom determining the amount of hapten in the human body fluid sample by reference to standard results.

10. A method according to claim 9, wherein the said hapten is digoxin.

* * * * *

UNITED STATES PATENT AND TRADEMARK OFFICE
CERTIFICATE OF CORRECTION

PATENT NO. : 4,427,781
DATED : January 24, 1984
INVENTOR(S) : Pierre L. Masson, Daniel Collet-Cassart and Carl G. Magnusson It is certified that error appears in the above-identified patent and that said Letters Patent are hereby corrected as shown below:

On the face page, left column, line 10, change "January 24, 1984" to --March 16, 1982--.

Signed and Sealed this

Tenth Day of April 1984

[SEAL]

Attest:

GERALD J. MOSSINGHOFF

Attesting Officer

Commissioner of Patents and Trademarks